United States Patent [19]

Ainsworth et al.

[11] Patent Number: 5,290,230
[45] Date of Patent: Mar. 1, 1994

[54] INTRALUMINAL CATHETER WITH A COMPOSITE SHAFT

[75] Inventors: Robert D. Ainsworth, Scotts Valley; Bruce H. Wand; David T. Jacobson, both of San Jose, all of Calif.

[73] Assignee: Advanced Cardiovascular Systems, Inc., Santa Clara, Calif.

[21] Appl. No.: 881,463

[22] Filed: May 11, 1992

[51] Int. Cl.⁵ .............................................. A61M 29/00
[52] U.S. Cl. .................................... 604/96; 604/282; 606/194
[58] Field of Search ................. 604/96, 95, 164, 165, 604/166, 169, 170, 280–283; 606/192–194

[56] References Cited

U.S. PATENT DOCUMENTS

| Re. 33,166 | 2/1990 | Samson . |
|---|---|---|
| 4,439,185 | 3/1984 | Lundquist . |
| 4,468,224 | 8/1984 | Enzmann et al. . |
| 4,516,972 | 5/1985 | Samson . |
| 4,538,622 | 9/1985 | Samson et al. . |
| 4,554,929 | 11/1985 | Samson et al. . |
| 4,582,181 | 4/1986 | Samson . |
| 4,619,263 | 10/1986 | Frisbie et al. . |
| 4,638,805 | 1/1987 | Powell . |
| 4,641,654 | 2/1987 | Samson et al. . |
| 4,664,113 | 5/1987 | Frisbie et al. . |
| 4,748,986 | 6/1988 | Morrison et al. . |
| 4,771,778 | 9/1988 | Mar . |
| 4,773,406 | 9/1988 | Spector et al. . |
| 4,793,350 | 12/1988 | Mar et al. . |
| 4,827,941 | 5/1989 | Taylor et al. . |
| 4,898,577 | 2/1990 | Badger et al. . |
| 4,966,163 | 10/1990 | Kraus et al. . |
| 4,981,478 | 1/1991 | Evard et al. . |
| 4,998,923 | 3/1991 | Samson et al. . |
| 5,057,338 | 10/1991 | Baucom et al. . |

*Primary Examiner*—John D. Yasko
*Attorney, Agent, or Firm*—Crosby, Heafey, Roach & May

[57] ABSTRACT

A composite tubular element for intravascular catheters, such as fixed-wire dilatation catheters and guiding and angiographic catheters, which is formed by braiding strands formed from an intimate mixture of polymeric matrix materials, such as fibers and powders, having a relatively low melting point and high strength reinforcing fibers having a relatively high melting point into a tubular element, heating the braided tubular element to melt the low melting point matrix materials and flow around the reinforcing fibers to form a matrix. A thermoplastic jacket or coating may then be extruded or otherwise applied to the exterior of the braided tubular element.

20 Claims, 3 Drawing Sheets

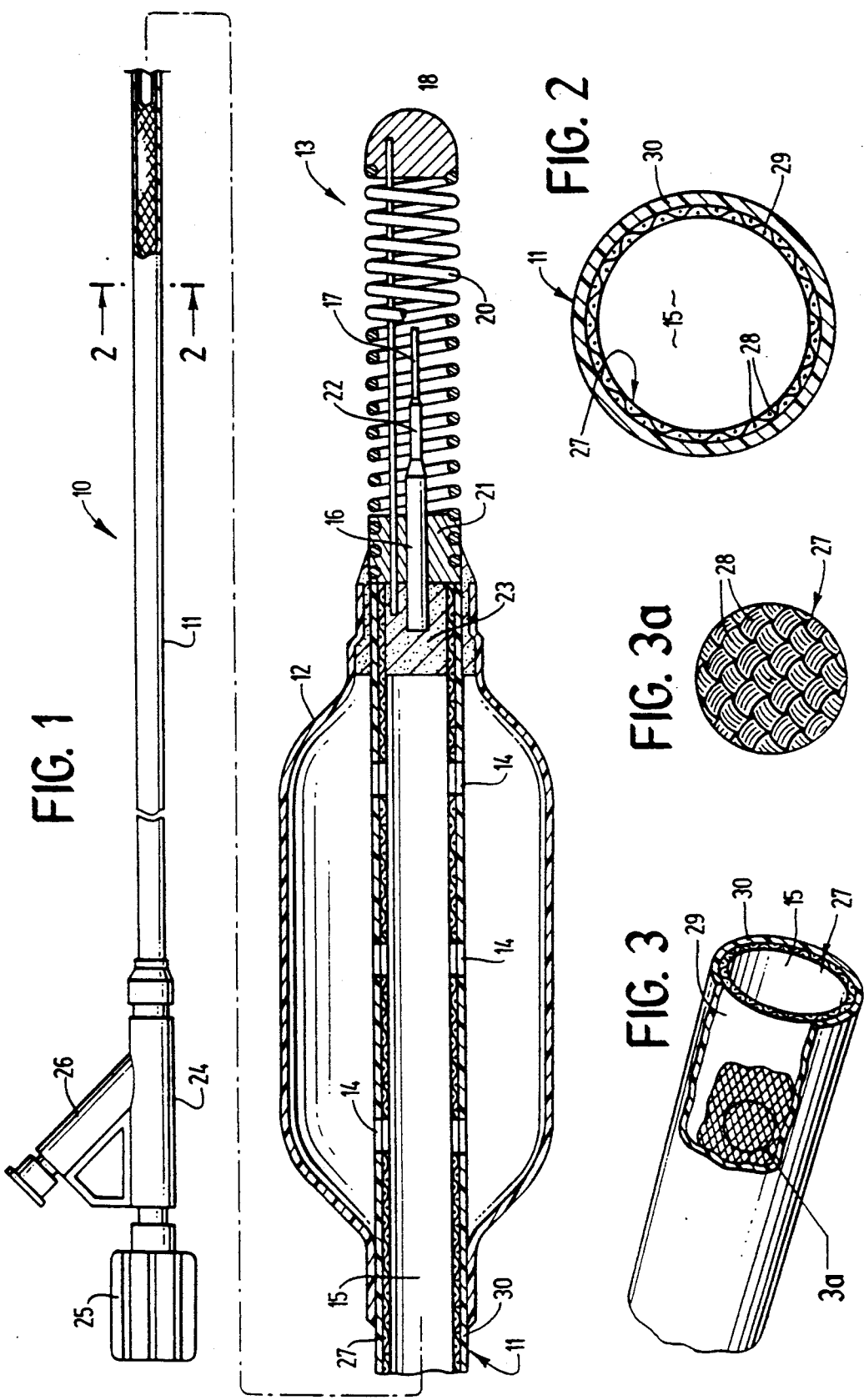

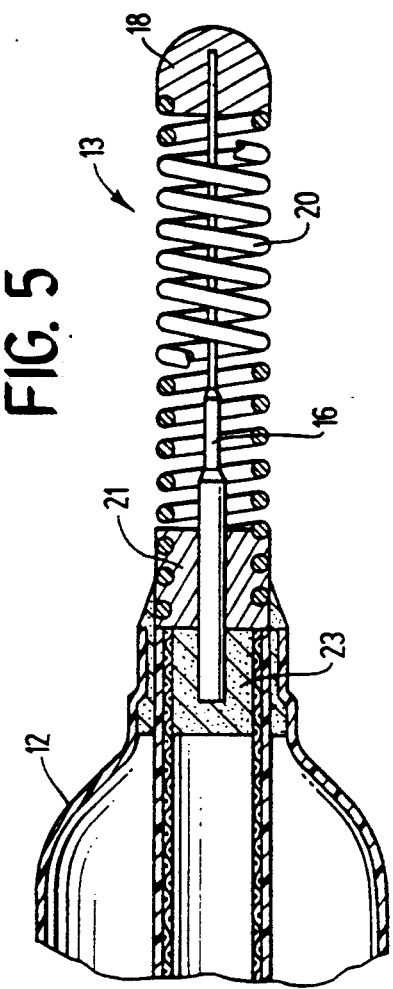
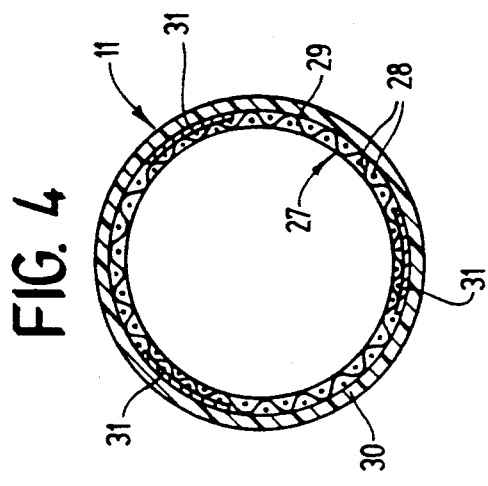
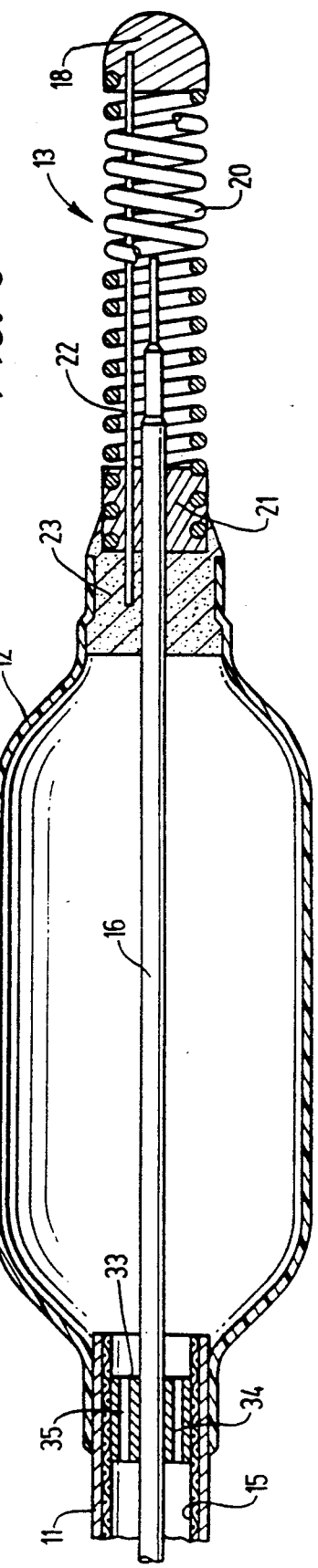

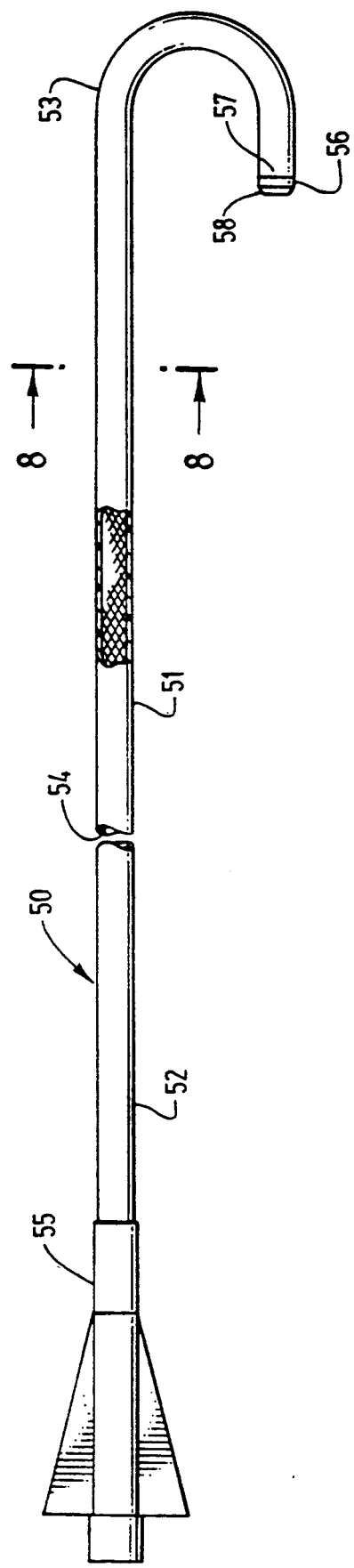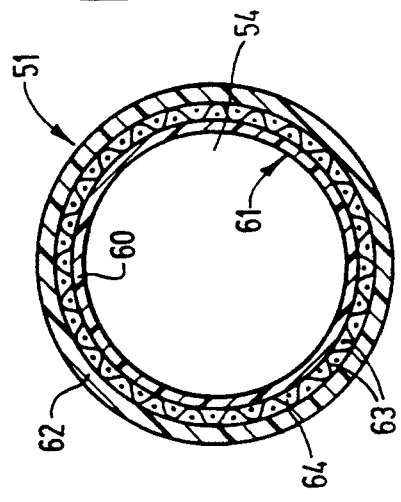

INTRALUMINAL CATHETER WITH A COMPOSITE SHAFT

BACKGROUND OF THE INVENTION

This invention generally relates to intraluminal catheters, such as guiding catheters and fixed-wire balloon dilation catheters used in percutaneous transluminal coronary angioplasty (PTCA).

In PTCA procedures, a guiding catheter having a preshaped distal tip is percutaneously introduced into the cardiovascular system of a patient and advanced therein until the preshaped distal tip of the guiding catheter is disposed within the aorta adjacent to the ostium of the desired coronary artery. The guiding catheter is twisted or torqued from the proximal end, which extends out of the patient, to turn the distal tip of the guiding catheter so that it can be guided into the desired coronary ostium. When utilizing a fixed-wire dilatation catheter in PTCA procedures, such as described and claimed in U.S. Pat. No. 4,582,181 (now U.S. Pat. No. Re. 33,166), the fixed-wire dilatation catheter is introduced into, and advanced through, the guiding catheter to the distal tip. Before the fixed-wire dilatation catheter is introduced into the guiding catheter, the distal tip of the dilatation catheter is usually manually shaped (curved) by the physician or one of the attendants. The fixed-wire dilatation catheter is advanced out the distal tip of the guiding catheter until the inflatable member on the distal extremity of the dilatation catheter extends across the lesion to be dilated. Once properly positioned across the lesion, the inflatable member is expanded to a predetermined size by inflation with radiopaque liquid at relatively high pressures (e.g., about 4-20 atmospheres) in order to dilate the stenosed region of the diseased artery. One or more inflations may be required to complete the dilatation of the stenosis. Dilatation of several stenoses in one patient can be performed with the same catheter. Upon the completion of the dilatations, the balloon is deflated so that the fixed-wire dilatation catheter can be removed from the dilated stenosis, and so that blood flow can resume through the dilated artery.

Further details of guiding catheters, fixed-wire dilatation catheters and other devices for angioplasty procedures can be found in U.S. Pat. No. Re. 33,166 (Samson); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,619,263 (Frisbie et al.); U.S. Pat. No. 4,638,805 (Powell); U.S. Pat. No. 4,641,654 (Samson et al.); U.S. Pat. No. 4,664,113 (Frisbie et al.); U.S. Pat. No. 4,748,986 (Morrison et al.); U.S. Pat. No. 4,771,778 (Mar); U.S. Pat. No. 4,793,350 (Mar et al.); U.S. Pat. No. 4,827,943 (Taylor et al.); U.S. Pat. No. 4,898,577 (Badger et al.); U.S. Pat. No. 4,966,163 (Kraus et al.); and U.S. Pat. No. 4,998,923 (Samson et al.), which are incorporated herein in their entirety by reference thereto.

Fixed-wire dilatation catheters for coronary angioplasty generally have an outer tubular member with an inflatable balloon on its distal portion which is capable of dilating a stenosis when the balloon is inflated to elevated pressures, and a shapable guiding member extending out through the distal end of the balloon which aids in directing the catheter to a desired branch artery where the stenosis to be dilated is located. The fixed-wire catheters usually have no inner tubular member and therefore usually have lower profiles, i.e. smaller transverse dimensions, than over-the-wire dilatation catheters having the same inflated balloon size. Moreover, because the fixed-wire catheters have the guidewire or guiding member fixed or at least restricted somewhat as to longitudinal movement, these catheters generally have greater pushability than over-the-wire type catheters of equivalent size. The lower profile and greater pushability of the fixed-wire dilatation catheters allows them to cross tighter lesions and to be advanced much deeper into a patient's coronary anatomy than the over-the-wire dilatation catheters of comparable sizes.

A major thrust in the development of materials and structure for intravascular catheters, such as balloon dilatation catheters, has been to reduce the profile or outer diameter of the catheter. The components of presently available dilatation catheters are usually made from homogeneous material, and the properties of available homogeneous materials suitable for catheter components have for the most part been pushed to the limit for these materials. In U.S. Pat. No. 4,981,478 (Evard et al.) composite catheter constructions are described which provide substantial improvements in catheter properties. However, notwithstanding the improvements made in properties of materials suitable for intravascular catheters, particularly fixed-wire dilatation catheters and guiding catheters for coronary use, a need remains for even greater improvements in property combinations which are not now available. The composite catheter construction of the present invention provides substantial improvements in properties and substantial reductions in transverse dimensions, and therefore responds to the aforesaid needs.

SUMMARY OF THE INVENTION

The present invention is directed to an improved catheter shaft construction which can be employed in a wide variety of intraluminal catheters, particularly guiding catheters and dilatation catheters used in angioplasty procedures.

The catheter shaft of the invention generally includes an elongated, tubular member of composite construction having an inner lumen extending therein. The composite tubular construction comprises braided, multifilament high strength polymer strands in a low melting point polymer matrix, with a jacket or coating, preferably of a thermoplastic polymer, provided on the exterior of the braided tubular member. The polymeric strands are multifilament and radially compressible. Presently preferred fibers for forming the strands are polymeric fibers such as aramid (e.g., Kelvar 49 sold by E. I. duPont, deNemours & Co.), polyester (e.g., Vectran sold by Hoechst-Celanese) and nylon. Preferred matrix polymer materials include polyethylene terephthalate, polyethylene terephthalate glycol and a polyester (e.g. Trevira by Hoechst-Celanese Corp).

The matrix material is preferably intimately mixed with the reinforcement fibers before the fibers are braided. In one preferred embodiment, the matrix material as fibers is incorporated into the reinforcement fibers. Other methods disperse the matrix material into the reinforcing fiber in the form of a finely divided powder. The amount of matrix material may range from about 40 to about 80%, preferably about 50 to about 70%, and the balance is high strength fibers. As used herein, all references to percent refer to weight percent, unless noted otherwise. The melting point of the matrix material must be less than the melting or decomposition temperature of the reinforcing fibers, but well above the temperatures to which the material is to be subsequently subjected, e.g., in packaging, sterilization and use. Melting points for suitable matrix materials will generally be above 120° C., but less that 270° C. whereas, suitable reinforcing fibers will have a melting point or a decomposition temperature, if the material does not melt, above 300° C.

Examples of incorporating matrix in powder form are described in U.S. Pat. No. 4,773,406 (Muzzy) and U.S. Pat. No. 5,057,338 (Baucom et al.), which are incorporated herein by reference. Such matrix powder/reinforcing strands are available in a wide variety of polymer combinations under the trademark TOWFLEX ® from Custom Composite Materials in Atlanta, Ga. The powdered matrix materials generally have discrete particles less than 50 microns, preferably less that 10 microns, in maximum dimension. Other means can be employed to form an incoherent dispersion of the matrix material within the fibrous stands.

A presently preferred method of forming the catheter shaft is to intimately mix the fibers of matrix material and reinforcing fibers in a desired ratio, forming the strands from the intimate mixture and then braiding a plurality of the strands about a suitable mandrel (e.g. a copper wire) into a tubular form with the reinforcing fibers in the desired location and orientation. The braided tubular structure is then passed through a heated chamber to melt the matrix fibers and to cause the melted matrix material to flow around the reinforcing fibers to form the matrix. The temperature employed is determined by the melting point of the matrix fiber material. The composite tubular member is then passed through an extrusion die where a thermoplastic jacket or coating is extruded onto the composite tubular member. The jacketed composite tubular member is cooled, e.g., by submersing the composite tubular member in a water trough located at the exit of the extrusion die. After cooling, the copper mandrel is removed. When forming the shaft for a guiding catheter, a thin inner tubular member formed of suitable lubricous material such as fluorinated ethylene propylene or polytetrafluoroethylene (e.g. Teflon ® sold by E.I. duPont deNemours & Co.) may be employed as the mandrel but in this instance the inner tubular member becomes part of the shaft and is not removed. The tube formed of lubricous material provides an inner lumen with very low frictional characteristics which is highly desireable in guiding catheters to facilitate the advancement of guidewires and dilatation catheters therethrough.

The method of forming the catheter shaft with reinforcing polymeric fibers having powdered matrix material dispersed within the fibers is essentially the same as described above when low melting point matrix fibers are incorporated into the high strength fibers.

To improve pushability without detrimentally affecting flexibility, wires or ribbons of suitable materials such as stainless steel and superelastic materials, such as NiTi (nickel-titanium) alloys commonly referred to as Nitinol TM, can be disposed within the walls of the composite catheter shaft and may extend straight or be helically disposed about the axis of the shaft. Details regarding the composition and methods for forming the superelastic wires and ribbons out of a presently preferred NiTi alloy can be found in copending application Ser. No. 07/629,381 filed Dec. 18, 1990, entitled SUPERELASTIC GUIDING MEMBER, which is hereby incorporated in its entirety by reference.

One presently preferred embodiment of the invention, which is directed to a fixed-wire dilatation catheter, comprises an elongated catheter shaft of composite construction having an inner lumen extending therein, an inflatable member, such as an inelastic balloon, on the distal extremity of the composite shaft having an interior in fluid communication with the inner lumen of the shaft and a flexible shapable distal tip which is secured to the distal extremity of the composite catheter shaft, and which extends distally from the distal end of the inflatable member. The flexible distal tip includes a core member and may also include a shaping ribbon. The distal end of the inflatable member is secured to the distal end of the composite shaft and the proximal end of the inflatable member is secured to the composite shaft at a location proximal to its distal end. An adapter is mounted onto the proximal end of the composite catheter shaft which is adapted to direct inflation fluid through the inner lumen of the catheter shaft into the interior of the inflatable member to effect the inflation thereof.

The composite shaft and inflatable member may also be employed as the outer tubular member in an over-the-wire type catheter which has at least in the distal portion an outer tubular member and an inner tubular member disposed within the outer tubular member and forming an annular inflation lumen with the outer tubular member. The inner tubular member is provided with a guidewire receiving inner lumen which extends to a guidewire port in the distal end of the inner lumen.

In another preferred embodiment, also directed to a fixed-wire dilatation catheter, the proximal end of the inflatable member is secured to the distal end of the composite shaft and the distal end of the inflatable member is secured to the flexible distal tip which is secured to the distal end of the composite shaft and extends out the distal end of the inflatable member. An aperture or port is provided in the distal end of the composite catheter shaft to allow inflation fluid from the inner lumen of the catheter shaft into the interior of the inflatable member.

In yet another presently preferred embodiment of the invention, a guiding catheter comprises an elongated shaft of the composite construction described above having an inner lumen extending therein. The distal portion of the catheter is given a shape (e.g., Judkins or Amplatz shapes) to facilitate the advancement and seating thereof within a desired coronary ostium and the distal tip is provided with a soft tip construction such as described in copending application Ser. No. 07/711,045, filed Jun. 6, 1991, entitled INTRAVASCULAR CATHETER WITH A NONTRAUMATIC DISTAL TIP, which is incorporated herein by reference.

The fixed-wire dilatation catheter of the invention has a very low deflated balloon profile combined with excellent pushability and longitudinal flexibility. The guiding catheter has excellent pushability and torquability. These and other advantages of the invention will become more apparent from the following detailed description of the invention when taken in conjunction with the accompanying exemplary drawings.

BRIEF DESCRIPTION OF THE DRAWINGS

FIG. 1 is a schematic elevational view, partially in section, of a fixed-wire dilatation catheter embodying features of the invention.

FIG. 2 is a transverse cross-sectional view of the dilatation catheter shown in FIG. 1 taken along the lines 2—2.

FIG. 3 is a perspective schematic view of the tubular shaft shown in FIG. 1 with the jacket partially removed to expose the underlying braided structure.

FIG. 3A is an enlarged view of the encircled area shown in FIG. 3.

FIG. 4 is a transverse cross-sectional view of a dilatation catheter similar to that shown in FIG. 1 with reinforcing ribbons incorporated into the wall of the shaft.

FIG. 5 is a longitudinal cross-sectional view of the distal portion of an alternate embodiment of the invention similar to that shown in FIG. 1 which has a core member extending to the distal tip of the coil but which does not have a separate shaping ribbon.

FIG. 6 is a longitudinal cross-sectional view of the distal portion of another alternative embodiment of the invention wherein the composite shaft terminates at the proximal end of the inflatable member.

FIG. 7 is a schematic, elevational view of a guiding catheter embodying features of the invention.

FIG. 8 is a transverse cross-sectional view of the guiding catheter shown in FIG. 7 taken along the lines 8—8.

DETAILED DESCRIPTION OF THE INVENTION

Reference is made to FIGS. 1 and 2 which schematically illustrate a fixed-wire dilatation catheter 10 embodying features of the invention. The catheter 10 includes an elongated catheter shaft 11 of composite construction, an inflatable balloon 12 mounted on the distal extremity of the shaft 11 and a flexible distal tip 13 secured to the distal end of the shaft 11. The distal portion of the catheter shaft 11, which is disposed within the interior of the inflatable member 12, is provided with a plurality of inflation ports 14 for directing inflation fluid from the inner lumen 15 extending within the catheter shaft to the interior of the balloon to inflate it.

The flexible distal tip 13 includes a core element 16 having a distal section 17 which terminates short of the rounded plug 18 on the distal end of the distal tip. A helical coil 20 is disposed about the core element 16 and is secured at its distal end to the rounded plug 18 by welding or other suitable means and at its proximal end to the core element 16 by solder, brazement or weld 21. A shaping ribbon 22, which is provided to facilitate shaping the distal tip 13, is secured by its proximal end to the core element 16 by solder or brazement 21 and by its distal end to the rounded plug 18 which is preferably formed by welding the distal tip of coil 20 to the distal tip of the shaping ribbon 22. The distal end of the balloon 12 and the distal end of the composite tubular shaft 11 are joined together to the proximal ends of the core element 16 and the ribbon 22 by adhesive 23. The proximal end of the composite shaft 11 extends through adapter 24 and is secured to the torquing knob 25 so that rotation of the knob will twist the shaft, and ultimately the flexible distal tip 13, in order to facilitate directing the catheter into a desired arterial branch. The shaft 11 is rotatable within the adapter 24. Inflation fluid is introduced into the inner lumen 15 through the side arm 26 of the adapter 24 which directs the fluid to the interior of the balloon 12.

FIG. 2 depicts the composite shaft 11 in transverse cross-section illustrating a braided tubular structure 27 formed of strands 28 of high strength reinforcing fibers in a matrix 29 of thermoplastic polymer. The exterior of the braided tubular structure 27 is provided with an outer coating or jacket 30, preferably formed of a thermoplastic polymer. The jacket 30 may be heat shrunk or otherwise suitably secured to the exterior of the braided tubular structure 27.

FIG. 3 illustrates the shaft 11 with the jacket 30 partially removed to shown the underlying braided structure with strands 28 formed of multifilament compressible fibers. FIG. 3A shows the interwoven nature of the braided tubular section 27 encircled in FIG. 3 on a larger scale.

An alternative catheter shaft construction is shown in FIG. 4 wherein reinforcing ribbons 31 are provided within the catheter shaft 11 to provide a greater degree of pushability and torquability with little loss in flexibility.

FIG. 5 illustrates a modification of the distal tip of the catheter shown in FIG. 1 wherein the shapable portion of the core member 16 extends to the distal end of the coil 20 and secured thereto by the rounded plug 18 which is formed by welding.

FIG. 6 illustrates another embodiment of the invention wherein the proximal end of the inflatable member 12 is suitably bonded, e.g., by adhesive, to the distal end of the composite catheter shaft 11 and the distal end of the inflatable member is suitably bonded by adhesive 23 to the core member 16 which extends through the interior of the inflatable member and out the distal end thereof. The proximal end of core member 16 is bonded by adhesive 34 to the distal end of the shaft 11 and extends to an intermediate location within the flexible distal tip 13. A shapable ribbon 22 extends from the distal end of the balloon to the distal end of the flexible distal tip 13 where it is suitably secured to the rounded plug 18. One or more lumens 34 and 35 are provided through the distal end of the shaft 11 to direct inflation liquid from the inner lumen 15 to the interior of balloon 12. This embodiment may also have the distal structure shown in FIG. 5 wherein the core member 16 has a shapable distal portion which is secured to the rounded plug 18. The fixed-wire catheter shown in FIG. 6 is otherwise the same as that shown in FIGS. 1 and 2 and corresponding parts are numbered the same.

In a typical embodiment of the invention, in the form of a fixed-wire catheter as shown in either FIGS. 1, 5 or 6, the braided tubular structure 27 has a wall thickness of about 0.003 inch (0.076 mm) and the outer jacket 30 has a wall thickness of about 0.001 inch (0.025 mm). The outer diameter of the composite catheter shaft 11 may range from about 0.025 to about 0.040 inch (0.6–1.0 mm). The overall length of the catheter 10 is usually from about 130 cm to about 150 cm unless an exchange of an over-the-wire dilation catheter is anticipated in which case the length would be typically about 175 cm.

The multifilament fibrous strands 28 employed to form the braided tubular structure 27 are preferably about 50 to about 250 denier and may be formed from a fibrous high strength polymer material including aramid (e.g. Kevlar 49) and a polyester such as Vectran TM. Other suitable polymeric materials may be employed. It is preferred to incorporate thermoplastic fibers or powder with the high strength fibrous strands 28 so that after the fibrous strands are braided into the braided tubular structure 27, the application of heat will melt the incorporated thermoplastic fibers or powder, causing it to flow around the high strength fibers 28 so that subsequent cooling will form the polymer matrix 29 into which the high strength polymer strands are imbedded. Suitable thermoplastic polymeric matrix materials include polyethylene, polyethylene terephthalate, polyethylene terephthalate glycol, and polyesters.

The inflatable members of the catheters may be balloons formed of a variety of relatively inelastic polymeric materials such as polyethylene, polyethylene terephthalate, polyvinyl chloride, and Surlyn ®. The inflatable member may also be formed as described in copending application Ser. No. 07/758,630, filed on Sep. 12, 1991, entitled BALLOON FOR VASCULAR CATHETERS which is incorporated herein in its entirety by reference thereto.

FIGS. 7 and 8 schematically illustrate a guiding or angiography catheter 50 of the invention which generally includes an elongated catheter shaft 51 having a proximal section 52, a more flexible distal section 53, an inner lumen 54 extending therein, a Luer hub 55 on the proximal end of the shaft and a nontraumatic distal tip 56 comprising two relatively short elastomeric tubular elements 57 and 58 which are coaxially disposed. The distal section 53 of the shaft 51 is shaped to facilitate the entry thereof into the ostium of a desired coronary artery. As will be appreciated by those skilled in the art, the J-shape of the distal section 53 of the catheter shown in FIG. 7 is a schematic representation and a variety of shapes, such as the well-known Judkins and Amplatz configurations for both the right and left coronary arteries, and may be employed to facilitate the entry of the distal tip of the guiding catheter into the ostium of the desired coronary artery. The relatively soft, nontraumatic distal tip 56 is intended to minimize traumatic engagement with arterial tissue.

FIG. 8 illustrates the composite construction of the shaft 51 of catheter 50. An optional thin-walled lubricous inner lining 60 is disposed within braided tubular element 61 and defines the inner lumen 54. The braided tubular element 61 has a coating or outer jacket 62, preferably formed of a thermoplastic polymeric material. The braided tubular element 61 is formed from a plurality of pairs of fibrous multifilament polymeric strands 63 within a matrix 64, as described above for the other embodiments, which are radially compressed against the inner liner 60 when they are braided. If an inner liner 60 is not employed, the tubular element is braided onto a removable mandrel.

The nontraumatic distal tip 56 of the catheter 50, as illustrated in FIG. 7, is comprised of two relatively short flexible tubular elements, a proximal element 57 and a distal element 58, and is butt joined to the distal end of shaft 51 by melt fusing or by a suitable adhesive, such as well-known cyanoacrylate-based adhesives, e.g. Loctite ™ 405 sold by Loctite Corporation, Newington, Conn. Both tubular elements 57 and 58 are formed of elastomeric or rubber-like materials but the distal section 58 is softer and more flexible than proximal section 57. Preferably, the proximal section 57 has a radiopaque filler material incorporated therein such as bismuth trioxide in order to make the distal tip fluoroscopically observable within a patient. Further details of guiding catheters, particularly with a non-traumatic distal tips, can be found in copending application Ser. No. 07/711,045, filed Jun. 6, 1991, which is incorporated in its entirety into the present application by reference thereto.

In one presently preferred embodiment of the invention, in the form of a guiding or angiography catheter, the inner lubricous lining 60 has a wall thickness of about 0.002 inch (0.051 mm), the braided tubular member 63 with the matrix 64 has a wall thickness of about 0.003 inch (0.076 mm) and the outer jacket 62 has a wall thickness of about 0.005 inch (0.13 mm). The diameter of the inner lumen 54 extending within the inner lining 60 may range from about 0.06 to about 0.09 inch (1.5-2.3 mm). The overall length of the catheter for coronary angioplasty may range from about 80 to about 125 cm.

As an example, the catheter shaft of the invention for the embodiment directed to guiding catheters is made by braiding 200 denier Vectran High Strength fibers commingled with 200 denier polyester fibers, sold by Hoechst-Celanese Corp. under the trademark Trevira, onto a 0.08 inch (2.03 mm) diameter mandrel formed of polytetrafluoroethylene with a braid angle of 45°. Approximately 500 feet of the braided tubular product was made. A reel of this braided tubular material was placed on a pultrusion/extrusion line and passed through a heating tube at a rate of several feet per second and at a temperature of about 250° C., causing the polyester fibers to melt and adhere to the Vectran fibers, thereby forming the composite matrix material. The heated material continued through the processing line to a crosshead-type extrusion die where melted polyurethane thermoplastic, Pellethane 55 D sold by the Dow Chemical Company, was coated onto the braided fiber composite structure to form a smooth outer surface with a hardness of about 55 Shore D durometer. After the extrusion, the coated composite structure was directed into a cooling water bath. The cooled composite structure was passed through a cutter which cut the tubular composite to a desired length, e.g. about 5 feet and the mandrel was then pulled out of the tubular composite material. One end of the composite tubular member, is heated and formed into the desired shape, e.g. Judkins or Amplatz shapes, and a conventional adapter is attached to the other end. The resulting composite shaft had an inner diameter of about 0.08 inch (2.03 mm) and an outer diameter of about 0.105 inch (2.67 mm).

While the invention has been describe herein primarily directed to intravascular catheters such as guiding or angiography catheters and fixed-wire dilatation catheters, those skilled in the art will recognize that the composite shaft of the present invention may be utilized in over-the-wire and rapid exchange type catheters and dilatation catheters with semimoveable guidewire. Additionally, it may be utilized in catheters adapted to be used in a wide variety of body lumens, e.g. balloon catheters for prostatic urethral dilation. Moreover, to the extent not specifically described herein, conventional materials and methods of manufacturing can be employed to form the catheters of the invention. Various modifications and improvements may be made to the invention without departing from the scope thereof.

What is claimed is:

1. A fixed-wire dilatation catheter for performing angioplasty procedures within a patient's arterial system comprising:
   a) a catheter shaft of braided composite construction having an inflation port in a distal portion thereof which has be formed by:
      braiding into a tubular structure a plurality of the compressible, multifilament strands which have dispersed therein a relatively low melting point polymeric matrix material, subjecting the braided tubular structure to sufficient heat to form a molten polymer matrix from the low melting point polymeric matrix material dispersed within the multifilament strands, and cooling the molten polymer matrix to a temperature below the melting point thereof;

b) a shapeable guide member which is secured to the distal end of the catheter shaft; and c) an inflatable member having proximal and distal ends with the proximal end being bonded to the catheter shaft at a location proximal to the inflation port and the distal end sealed about the shapeable guide member which extends therethrough.

2. The dilatation catheter of claim 1 wherein the composite shaft has a plurality of reinforcing ribbons extending parallel to each other within a wall of the shaft.

3. The dilatation catheter of claim 2 wherein at least three reinforcing ribbons are helically disposed within the wall of the composite shaft and are selected from the group consisting of stainless steel and superelastic NiTi alloy.

4. The dilatation catheter of claim 1 wherein a thermoplastic coating or jacket is provided on the exterior of the composite shaft having a thickness of about 0.0005 to about 0.002 inch.

5. The dilatation catheter of claim 1 wherein the flexible distal tip includes a core member which is secured to the distal end of the catheter shaft.

6. The dilatation catheter of claim 5 wherein a shapeable ribbon is secured by its proximal end to the distal end of the composite shaft.

7. The dilatation catheter of claim 6 wherein the flexible distal tip has a helical coil disposed about the core member and about the ribbon and the ribbon is secured by its distal end to the distal end of the coil.

8. The dilatation catheter of claim 5 wherein the flexible distal tip is provided with a helical coil disposed about the core member and the core member is secured by its distal end to the distal end of the of the coil.

9. The dilatation catheter of claim 1 wherein the catheter shaft is formed of a braided high strength polymeric fiber in a low melting point thermoplastic polymer matrix.

10. A method of forming a small diameter flexible composite shaft, comprising:
a) braiding into a tubular structure a plurality of the compressible, multifilament strands which have dispersed therein a relatively low melting point polymeric matrix material;
b) subjecting the braided tubular structure to sufficient heat to form a molten polymer matrix from the low melting point polymeric matrix material dispersed within the multifilament strands; and
c) cooling the molten polymer matrix to a temperature below the melting point thereof.

11. The method of claim 10 wherein the amount of matrix material ranges from about 40% to about 80% (by wt).

12. The method of claim 10 wherein the polymeric matrix material is dispersed into the high strength fibers in the form of fibers or powder.

13. The method of claim 10 wherein the reinforcing fibers are selected from the group consisting of aramid, nylon and polyesters.

14. The method of claim 10 wherein the polymeric matrix material is a low melting point thermoplastic polymer selected from the group consisting of polyester, polyethylene terephthalate and polyethylene terephthalate glycol and mixtures thereof with other polymer materials.

15. A composite flexible small diameter tubular member comprising a relatively low melting point thermoplastic polymer matrix with braided high strength polymeric reinforcing strands disposed within the matrix, said tubular structure having been formed by,
a) braiding into a tubular structure a plurality of the compressible, multifilament strands which have dispersed therein a relatively low melting point polymeric matrix material;
b) subjecting the braided tubular structure to sufficient heat to form a molten polymer matrix from the low melting point polymeric matrix material dispersed within the multifilament strands; and
c) cooling the molten polymer matrix to a temperature below the melting point thereof.

16. The guiding or angiography catheter of claim 15 including a soft distal tip to prevent or minimize traumatic engagement with blood vessel lining.

17. A balloon catheter for performing diagnostic or therapeutic procedures within a patient's body lumen, comprising:
a) an elongated catheter shaft having proximal and distal ends and having outer tubular member with a braided composite construction with an inflation port in a distal portion thereof;
b) a shapable guide member which is secured to the distal end of the catheter shaft; and
c) an inflatable member having proximal and distal ends with the proximal end of the inflatable member being bonded to the catheter shaft at a location proximal to the inflation port and with the distal end sealed about the shapable guide member which extends therethrough.

18. A guiding or angiography catheter for performing diagnostic or therapeutic procedures within a patient's arterial system comprising a catheter shaft of braided composite construction and formed of a relatively low melting point polymeric matrix with braided high strength reinforcing polymeric strands disposed within the matrix, said catheter having been formed by;
a) braiding into a tubular structure a plurality of the compressible, multifilament strands which have dispersed therein a relatively low melting point polymeric matrix material;
b) subjecting the braided tubular structure to sufficient heat to form a molten polymer matrix from the low melting point polymeric matrix material dispersed within the multifilament strands; and
c) cooling the molten polymer matrix to a temperature below the melting point thereof.

19. The dilatation catheter of claim 17 wherein at least three reinforcing ribbons are helically disposed within the wall of the composite shaft.

20. The dilatation catheter of claim 17 wherein the reinforcing ribbons are formed of a material selected from the group consisting of stainless steel and superelastic NiTi alloy.

* * * * *